US005730910A

United States Patent [19]
Antkowiak

[11] Patent Number: 5,730,910
[45] Date of Patent: Mar. 24, 1998

[54] METHOD FOR PREPARING POLYMETALATED COMPOSITIONS

[75] Inventor: Thomas A. Antkowiak, Rittman, Ohio

[73] Assignee: Bridgestone/Firestone, Inc., Akron, Ohio

[21] Appl. No.: 778,924

[22] Filed: Jan. 3, 1997

[51] Int. Cl.⁶ ............................................. C07F 1/02
[52] U.S. Cl. ................... 260/665 R; 526/335; 526/340
[58] Field of Search ............... 260/665 R; 526/340, 526/335

[56] References Cited

U.S. PATENT DOCUMENTS

| | | | |
|---|---|---|---|
| 3,159,587 | 12/1964 | Uraneck et al. | 252/431 |
| 3,193,590 | 7/1965 | Hsieh | 260/665 |
| 3,296,150 | 1/1967 | Kable | 252/431 |
| 3,303,225 | 2/1967 | Hsieh et al. | 260/665 |
| 3,410,918 | 11/1968 | Beumel et al. | 260/665 |
| 3,975,453 | 8/1976 | Smith | 260/665 R |
| 4,339,397 | 7/1982 | Ishihara et al. | 260/665 R |
| 5,062,998 | 11/1991 | Herman et al. | 260/665 R |
| 5,080,835 | 1/1992 | Kang | 250/665 R |
| 5,147,951 | 9/1992 | Kang et al. | 526/173 |
| 5,231,152 | 7/1993 | Roggeman et al. | 526/173 |
| 5,260,370 | 11/1993 | Kang et al. | 524/575 |
| 5,272,203 | 12/1993 | Joyner et al. | 524/575 |
| 5,489,660 | 2/1996 | Roggeman et al. | 526/340 |

OTHER PUBLICATIONS

Eberly et al, J. Organometal. Chem., 3 (1965), pp. 165–167.
Adams et al, Kautschuk und Gummi, Kunstoffe 18. Jahrgang, pp. 709–715, Nr, Nov. 1965.
Makowski et al, J. Macromol. Sci, Chem., E2(4) pp. 683–700, Jul. 1968.
Masuda et alf, Macromolecules, vol. 20, No. 7, (1987) pp. 1467–1487.

*Primary Examiner*—Paul F. Shaver

[57] ABSTRACT

A method of preparing polymetalated compositions and the use of such polymetalated compounds as catalysts in polymerization reactions are described. The process comprises reacting (A-1) an allenic compound of the formula $R^2$—$CH$=$C$=$CH_2$ wherein $R^2$ is hydrogen or an aliphatic group containing from 1 to about 10 carbon atoms with (A-2) an organometallic compound $R^oM$ in a mole ratio of about 1:2 to about 1:6 wherein $R^o$ is a hydrocarbyl group and M is an alkali metal.

A method of preparing a hydrocarbon-soluble polymetalated compositions also is described, and this process comprises the steps of (A) preparing an intermediate by reacting (A-1) an allenic compound of the formula $R^2$—$CH$=$C$=$CH_2$ wherein $R^2$ is hydrogen or an aliphatic group containing from 1 to about 10 carbon atoms with (A-2) an organometallic compound $R^oM$ in a mole ratio of about 1:2 to about 1:6 wherein $R^o$ is a hydrocarbyl group and M is an alkali metal; and (B) reacting said intermediate with a 1,3-conjugated diene wherein the mole ratio of the 1,3-conjugated diene to the allenic compound is at least about 2:1.

The hydrocarbon-soluble polymetalated compositions prepared by the method of the present invention are useful as catalysts in anionic polymerizations.

28 Claims, No Drawings

METHOD FOR PREPARING POLYMETALATED COMPOSITIONS

TECHNICAL FIELD OF THE INVENTION

This invention relates to a novel method of preparing polymetalated compositions from allenic compounds. More particularly, this invention relates to such compositions containing two, three or four alkali metal substituents per molecule. The compositions are useful as catalysts in anionic polymerizations.

BACKGROUND OF THE INVENTION

Polymetalated 1-alkyne compositions have been described in U.S. Pat. No. 5,080,835, and the polymetalated 1-alkyne compositions comprise the reaction product of a 1-alkyne, an organometallic compound ($R^oM$ wherein $R^o$ is a hydrocarbyl group and M is an alkali metal), and a 1,3-conjugated diene. The mole ratio of conjugated diene to 1-alkyne is at least about 2:1. The compositions described in the '835 patent are characterized by the formula

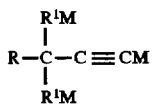

wherein R is hydrogen, a hydrocarbyl group or $R^1M$, M is an alkali metal, $R^1$ is a divalent oligomeric hydrocarbyl group comprising moieties derived from a conjugated diene, and wherein the total number of moieties derived from a conjugated diene in all of the $R^1$ groups in Formula I is from about 2 to about 30.

Other alkali metal acetylides have been described in the literature and various procedures for preparing such acetylides from alkyne compounds have been suggested. Among the publications describing such reactions are U.S. Pat. No. 3,303,225; Eberly and Adams, *J. Organometal. Chem.*, 3 (1965) 165-167; H. E. Adams et al, *Kautschuk und Gummi, Kunstoffe* 18.*Jahrgana*, pp. 709-716, Nr, 11/1965; Makowski et al, *J. Macromol. Sci.- Chem.*, E2(4) pp. 683-700, July, 1968; Masuda et al, *Macromolecules*, Vol. 20, No. 7, (1987) pp. 1467-1487.

U.S. Pat. No. 3,410,918 describes the preparation of propynyl sodium and propynyl lithium. The process involves contacting a gaseous mixture of propyne and allene in a weight ratio of 1:1 to 4:1 with a slurry of sodium metal or lithium metal in an inert ether type solvent or in certain aromatic and aliphatic hydrocarbons solvents.

U.S. Pat. No. 3,975,453 describes a process for preparing butynyl lithium by passing an unsaturated hydrocarbon selected from the group consisting of 1,2-butadiene, or a mixture of 1,2-butadiene, 1,3-butadiene, 1-butyne and 2-butyne into a slurry of finely divided lithium metal dispersed in a strong coordinating ether solvent.

U.S. Pat. No. 4,339,397 describes a process for preparing the sodium salt of a 1-alkyne of the general formula $R^1R^2C$(H)C≡CNa by the reaction of a corresponding 1,2-alkadiene with sodium metal in an inert organic solvent.

SUMMARY OF THE INVENTION

A method of preparing polymetalated compositions and the use of the polymetalated composition as catalysts in polymerization reactions are described. The process comprises reacting (A-1) an allenic compound of the formula $R^2$—CH=C=$CH_2$ wherein $R^2$ is hydrogen or an aliphatic group containing from 1 to about 10 carbon atoms with (A-2) an organometallic compound $R^oM$ in a mole ratio of about 1:2 to about 1:6 wherein $R^o$ is a hydrocarbyl group and M is an alkali metal.

A method of preparing hydrocarbon-soluble polymetalated compositions also is described, and this process comprises the steps of (A) preparing an intermediate by reacting (A-1) an allenic compound of the formula $R^2$—CH=C=$CH_2$ wherein $R^2$ is hydrogen or an aliphatic group containing from 1 to about 10 carbon atoms with (A-2) an organometallic compound $R^oM$ in a mole ratio of about 1:2 to about 1:6 wherein $R^o$ is a hydrocarbyl group and M is an alkali metal; and (B) reacting said intermediate with a 1,3-conjugated diene wherein the mole ratio of the 1,3-conjugated diene to the allenic compound is at least about 2:1.

The hydrocarbon-soluble polymetalated compositions prepared by the method of the present invention are useful as catalysts in anionic polymerizations.

DESCRIPTION OF THE PREFERRED EMBODIMENTS

A first embodiment of the present invention is a process for preparing polymetalated compositions comprises the steps of reacting (A-1) an allenic compound of the formula $R^2$—CH=C=$CH_2$ wherein $R^2$ is hydrogen or an aliphatic group containing from 1 to about 10 carbon atoms with (A-2) an organometallic compound $R^oM$ in a mole ratio of about 1:2 to about 1:6 wherein $R^o$ is a hydrocarbyl group and M is an alkali metal. The polymetalated compositions of the first embodiment are sometimes referred to herein as "intermediates" since they can be further reacted with a 1,3-diene compound.

A second embodiment of the present invention is a process for preparing hydrocarbon-soluble polymetalated compositions comprises the steps of (A) preparing an intermediate by reacting (A-1) an allenic compound of the formula $R^2$—CH=C=$CH_2$ wherein $R^2$ is hydrogen or an aliphatic group containing from 1 to about 10 carbon atoms with (A-2) an organometallic compound $R^oM$ in a mole ratio of about 1:2 to about 1:6 wherein $R^o$ is a hydrocarbyl group and M is an alkali metal; and (B) reacting said intermediate with a 1,3-conjugated diene wherein the mole ratio of the 1,3-conjugated diene to the allenic compound is at least about 2:1.

The compositions prepared by the process of the second embodiment are sometimes referred to herein as the "diene-modified" polymetalated compositions.

The allenic compounds used in the processes of this invention are characterized by the formula

wherein $R^2$ is hydrogen or an aliphatic group containing from one to about 10 carbon atoms. More often, $R^2$ is an aliphatic group containing from 1 to about 4 carbon atoms. Representative examples of such allenic compounds include allene (1,2-propadiene), 1,2-butadiene; 1,2-pentadiene; 1,2-hexadiene; 1,2-heptadiene; 1,2-octadiene, etc.

The organometallic compound is represented by the formula $R^oM$ wherein $R^o$ is a hydrocarbyl group which may be a saturated aliphatic group, a saturated cycloaliphatic group, or an aromatic group. Generally, $R^o$ will contain up to about 20 carbon atoms. M is an alkali metal including lithium, sodium, potassium, rubidium, cesium and francium. Representative examples of the organometallic compound $R^oM$ include: methylsodium, ethyllithium; propyllithium;

isopropylpotassium, n-butyllithium, s-butyllithium; t-butylpotassium; t-butyllithium; pentyllithium; n-amylrubidium; tert-octyl-cesium; phenyllithium; naphthyllithium; etc.

The mole ratio of R°M to allenic compound is between about 2:1 and about 6:1, more often from about 3:1 to about 5:1.

The reaction of the allenic compound with the organometallic compound (followed by reaction with the 1,3-conjugated diene) can be carried out in the presence of an inert diluent, and particularly, in the presence of a hydrocarbon such as an aliphatic, cycloaliphatic or aromatic hydrocarbon. Representative examples of suitable hydrocarbon diluents include n-butane, n-hexane, isooctane, decane, dodecane, cyclohexane, methylcyclohexane, benzene, etc. Preferred hydrocarbons are aliphatic hydrocarbons containing from four to about 10 carbon atoms per molecule. Mixtures of hydrocarbons can also be utilized.

The number of metal substituents introduced into the compositions of the present invention will depend primarily upon the type of allenic compound, and the relative amounts of the allenic compound and the organometallic compounds present in the initial reaction. Although not wishing to be bound by any theory, it is believed that when the organometallic compound reacts with the allenic compound on an equimolar basis, either or both of the following reactions may occur.

(1) $R^2—CH=C=CH_2 + R°M \rightarrow R^2CH_2C\equiv CM + R°H$ (2) $R^2CH=C=CH_2 + R°M \rightarrow R^2CH=CH=CHM + R°H$ In the first reaction, the allenic compound rearranges to a 1-alkyne. It is presently believed that reaction (1) is the predominating reaction.

If two moles of R°M are reacted with one mole of the allenic compound, the intermediate formed can be represented by the formulae $R^2CH(M)C\equiv CM$ and/or $R^2C(H)=C=C(M)_2$, and if three moles are reacted, the intermediate formed can be represented by the formulae $R^2—C(M)_2—C\equiv CM$ or $R^2C(M)=C=C(M)_2$. When $R^2$ is hydrogen, four moles of R°M can react, and the structure of the intermediate can be represented by $M_2C=C=CM_2$ and/or $M_3C—C\equiv CM$. The intermediate formed when one mole of the allenic compound is reacted with more than 2 moles of R°CM is presently believed to comprise a mixture of polymetalated 1-alkynes and polymetalated allenes, along with unreacted R°M.

The reaction between the allenic compound and the organometallic compound to form the intermediate can be effected at temperatures of 20°–80° C., and the reaction is generally conducted in an inert atmosphere such as under nitrogen. The reaction generally is conducted at atmospheric pressure. The intermediate obtained from this reaction is believed to be a mixture of polymetalated alkynes and/or polymetalated allenes which are either insoluble or only slightly soluble in hydrocarbons. The presence of unreacted R°M is believed to promote solubility of the mixtures of polymetalated compounds.

The polymetalated compositions prepared by the above process of the invention (first embodiment) may be characterized as comprising a mixture of at least one polymetalated 1-alkyne and at least one polymetalated allene. The polymetalated 1-alkynes can be characterized by the formula

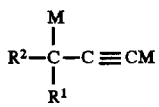

wherein $R^2$ is hydrogen, a hydrocarbyl group or M, $R^1$ is hydrogen or M, and M is an alkali metal. The allene compounds in the mixture can be represented by the formula

wherein $R^2$ is hydrogen, a hydrocarbyl group or M, and $R^1$ is hydrogen or M, and M is an alkali metal. The amounts of the various polymetalated compounds in the compositions of the first embodiment of the invention is not presently known.

In a second embodiment of the invention, the above-described intermediate is reacted with a 1,3-conjugated diene. The reaction between the intermediate and a 1,3-conjugated diene forms a hydrocarbon soluble, diene-modified product and the reaction generally is conducted at a temperature above 50° C. and more generally at a temperature of from about 70° C. to about 150° C. The reaction generally is completed in less than about 5 hours. At about 80° C. the reaction is completed in about 2 hours. At higher temperatures, the reaction is completed in less than 2 hours. If the reaction mixture is heated for too long a period, the catalytic activity of the resulting product may be reduced. The product of this reaction is a hydrocarbon-soluble polymetalated composition believed to comprise one or more polymetalated 1-alkynes and, one or more polymetalated allenic compounds, wherein the alkynes and allenes contain one or more divalent oligomeric hydrocarbyl groups comprising moieties derived from the 1,3-conjugated diene. The mole ratio of 1,3-conjugated diene to the allenic compound reacted with the intermediate is at least about 2:1 and may be as high as 30: 1. In one preferred embodiment, the mole ratio of conjugated diene to allenic compound is in a range of from about 8:1 to about 20:1.

The 1,3-conjugated dienes may be any of a variety of 1,3-conjugated dienes including those containing from four to 12 carbon atoms, and preferably from four to eight carbon atoms per molecule. Specific examples of the 1,3-conjugated dienes include: 1,3-butadiene; isoprene; 2,3-dimethyl-1,3-butadiene; 1,3-pentadiene(piperylene); 2-methyl-3-ethyl-1, 3-butadiene; 3-methyl-1,3-pentadiene; 1,3-hexadiene; 2-methyl-1,3-hexadiene; 1,3-heptadiene; 1,3-octadiene; etc. In one preferred embodiment, the 1,3-conjugated dienes are 1,3-butadiene, isoprene or 1,3-pentadiene.

In the second embodiment of the invention, the polymetalated diene-modified compositions may be characterized as comprising at least one polymetalated 1-alkyne and at least one polymetalated allene. The hydrocarbon-soluble polymetalated 1-alkynes can be characterized by the formula

wherein $R^2$ is hydrogen, a hydrocarbyl group or $R^3M$, $R^4$ is hydrogen or $R^3M$, M is an alkali metal and $R^3$ is a divalent oligomeric hydrocarbyl group comprising moieties derived from a conjugated diene. The hydrocarbon-soluble allenes may be characterized by the formula

wherein $R^2$ is hydrogen, a hydrocarbyl group or $R^3M$, $R^4$ is hydrogen or $R^3M$, M is an alkali metal and each $R^3$ is independently a divalent oligomeric hydrocarbyl group comprising moieties derived from a conjugated diene.

As noted, $R^2$ may be hydrogen or a hydrocarbyl group which may be a saturated aliphatic, saturated cycloaliphatic or an aromatic group generally containing up to about 10 carbon atoms. In one embodiment, $R^2$ is an alkyl group containing from 1 to 5 carbon atoms. In a further embodiment $R^2$ is a methyl group. M is an alkali metal including lithium, sodium, potassium, rubidium, cesium and francium. Lithium, sodium and potassium are preferred alkali metals, and lithium is the most preferred alkali metal, particularly when the polymetalated compositions are to be used as polymerization catalysts.

The substituents $R^3$ in Formulae III and IV are divalent oligomeric hydrocarbyl groups comprising moieties derived from a 1,3-conjugated diene as described above. The number of moieties derived from a conjugated diene in the $R^3$ groups of the composition of Formulae III and IV may be varied over a range of from two to about 30. Generally, the total number of moieties derived from a conjugated diene in all of the $R^3$ groups in the composition of Formulae III and IV is from about 2 to about 30. In one preferred embodiment, the total number of conjugated diene derived moieties in all of the $R^3$ groups in the composition of Formulae III and IV is from about eight to about 20. The number of moieties derived from a conjugated diene in the oligomeric groups $R^3$ can be varied to provide compositions having a weight average molecular weight of from about 200 to about 3000. In one preferred embodiment, the weight average molecular weight of the compositions is within a range of from about 500 to about 1500.

The polymetalated compounds prepared by the process of this invention contain active as well as inactive metal. The presence of at least two different types of carbon metal linkages in the compositions of this invention can be shown by both chemical and physical evidence. Gilman titration with allyl bromide distinguishes between metal acetylide (—C≡C—M) which is inactive and other carbon lithium linkages (—C—C—M) which are active. Titration of the compositions prepared by the process of this invention show 50%, 67% and 75% of the total carbon-metal linkages are "active" corresponding to di-, tri-, and tetra-metalated alkynes. Ultraviolet and visible spectral studies show peak absorbances at 300–340 NM and 400–450 NM for the compositions of this invention corresponding to inactive and active metal linkages, respectively.

An important property of these compositions that have been reacted with a 1,3-diene is that they are soluble in hydrocarbon solvents, and the solutions are stable at room temperature for an extended period of time. The terms "soluble in hydrocarbon solvent" or "hydrocarbon-soluble" as used in the specifications and claims indicate that the materials are soluble in hydrocarbons to the extent of at least about 5 g per 100 g of solvent, particularly an aliphatic solvent such as hexane, at temperatures of about 25° C. The compositions are useful as catalysts in the anionic polymerization and copolymerization of various hydrocarbon monomers.

The following examples illustrate the process of the invention for preparing the polymetalated intermediates and the process for preparing the hydrocarbon-soluble polymetalated compositions. Unless otherwise indicated in these examples and elsewhere in the specification and claims, all parts and percentages are by weight, temperatures are in degrees centigrade and pressure is at or near atmospheric pressure.

In each of the following examples, the 1,2-butadiene source is a mixture of 1,2-butadiene and cis-butene-2. The cis-butene-2 is unreactive with n-butyllithium.

Preparation of Intermediates

EXAMPLE A

A mixture of 96 mL of a 1.6 M solution of n-butyllithium in hexane, and 6.3 grams of a mixture containing 43% 1,2-butadiene and 55.2% of cis-butene-2 is prepared at room temperature under a nitrogen atmosphere in a 28 oz. beverage bottle equipped with a rubber liner, 3-hole crown cap and magnetic stirrer. The molar ratio of n-butyllithium to 1,2-butadiene is 3.06: 1. The mixture is tumbled in a 65° C. constant temperature bath for 3.0 hours. A small sample of the red, clear solution is removed to analyze for n-butyllithium. In one test, a gas chromatographic analysis for BuSiMe$_3$ after reaction with ClSiMe$_3$ indicates that 71% of the n-butyllithium has reacted. A Gilman titration on another small sample indicates an active carbon-lithium linkage of 67.9%.

EXAMPLES B–F

The procedure of Example A is repeated at 65° C. and at 80° C. for periods of from about 0.5 to about 7 hours. The amount of n-butyllithium remaining at the end of each reaction is determined and is summarized in the following table.

| Example | Hrs. at 65° C. | % BuLi Remaining |
|---|---|---|
| B | 5.0 | 23–25 |
| C | 7.0 | 21–23 |

| Example | Hrs. At 80° C. | % BuLi Remaining |
|---|---|---|
| D | 0.5 | 31 |
| E | 1.0 | 26–27 |
| F | 2.0 | 21 |

Preparation of Diene-Modified Polymetalated Compositions

EXAMPLE 1

To a nitrogen-filled and capped 28 oz. beverage bottle is added 96 mL of a 1.6 M n-butyllithium solution (153.6 mM) in hexane and 6.3 grams of a mixture of 43.0% of 1,2-butadiene and 55.2% cis-butene-2. This mixture is tumbled for 45 minutes at 50° C. and for 5 hours at 65° C. in a constant temperature bath. Analysis of the intermediate thus obtained indicates 75 % of the n-butyllithium as reacted and the intermediate contains an active carbon-lithium linkage of 66.7% (by Gilman titration).

To the above mixture (intermediate), there is added 120.8 grams of a blend of 1,3-butadiene in hexane containing 23.5% of 1,3-butadiene. The mole ratio of 1,3-butadiene to 1,2-butadiene is 10.5:1. This mixture is tumbled at 65° C. for 25 minutes and at 80° C. for 2 hours to form the desired product which is cooled to room temperature and stored.

EXAMPLE 2

To a 10-gallon nitrogen-filled stainless steel reactor is added about 3200 grams of hexane, 694.8 grams of a mixture of 45.7% of 1,2-butadiene and 54% cis-butene-2 and about 7.67 kg. of 15% solution of n-butyllithium in hexane. This mixture is stirred at room temperature for 30 minutes. A blend of about 9.6 kg. of 1,3-butadiene (33%) in hexane (mole ratio of 1,3-butadiene to 1,2-butadiene 10:1) is then added and this mixture is heated by increasing the jacket temperature to about 85° C. (185° F.) and maintained at this temperature for 2 hours. The desired product is obtained and cooled to room temperature.

EXAMPLE 3

To a 10-gallon, nitrogen-filled stainless steel reactor is added 3.2 kg. of hexane, 694.8 grams of a mixture of 45.7% of 1,2-butadiene, and 54% cis-butene-2 and 7.67 kg. of 15% solution of n-butyllithium in hexane. This mixture is stirred at about 65° C. for 3 hours and then cooled to about 32° C. A blend of 1,3-butadiene (33% in hexane (9.62 kg.)) is added, (mole ratio of 1,3-butadiene to 1,2-butadiene is 10:1) and this mixture is stirred at about 71° C. (160° F.) for about 2 hours. The product is cooled to room temperature.

The hydrocarbon-soluble, diene-modified polymetalated compositions prepared by the method of the present invention are stable for an extended period at room temperature. For example, the polymetalated compositions can be stored at room temperature under a nitrogen atmosphere for up to six months or more without significant loss of their activity as catalysts for anionic polymerization reactions.

The polymetalated diene-modified compositions are useful as catalysts for the anionic polymerization of a variety of hydrocarbon monomers including olefins such as ethylene, styrene, α-methylstyrene, divinylbenzene and alkyl-substituted styrenes; and dienes such as butadiene, isoprene, piperylene and 2,3-dimethylbutadiene. The catalysts also may be utilized for preparing copolymers or mixtures containing two or more of the above olefins, dienes, or mixtures thereof. The polymers and copolymers obtained in this manner contain alkali metal, and polymers of these types have been referred to as "living polymers." The "live ends" of the polymers (i.e., the carbon-alkali metal bonds) can be used to couple the polymers or to introduce terminal, functional groups such as silane, hydroxyl, carboxyl, mercapto, amino, substituted tin, etc., by procedures well known to those skilled in the art.

The polymetalated diene-modified compositions prepared by the process of the present invention are useful particularly as catalysts for the preparation of copolymers of a 1,3-conjugated diene monomer and an aromatic vinyl monomer. The relative amounts of conjugated diene and aromatic vinyl monomers included in the copolymers may be varied over a wide range depending upon the desired copolymer properties. Thus, the amount of conjugated diene in the copolymer may vary from about 10% to about 90% by weight, and the amount of aromatic vinyl compound may vary from about 10% to about 90% by weight. More generally, the copolymers will comprise from about 50% to about 90% by weight, preferably from about 50% to about 80% by weight of the conjugated diene and from about 10% to about 50% by weight, more preferably from about 20% to about 50% by weight of the aromatic vinyl compound. The copolymers may have weight average molecular weights of at least about 300,000.

In one embodiment, the copolymers which can be prepared with the catalyst prepared in accordance with the method of the present invention are of the type generally referred to as ultra-high molecular weight copolymer compositions. The ultra-high molecular weight copolymer compositions are essentially free of gel and are further characterized as having a weight average molecular weight of greater than about 500,000 and even greater than about 1,000,000. High molecular weight copolymer compositions can be prepared with the catalyst described herein having a weight average molecular weight of greater than 1,100,000. Other characterizing features of the ultra-high molecular weight polymers prepared with the catalyst of the present invention include inherent viscosity, dilute solution viscosity and percent relaxation as determined using a Mooney viscometer. In one embodiment, the copolymer compositions prepared with the catalysts described herein are characterized as having an intrinsic viscosity in tetrahydrofuran of at least 4.0, and in another embodiment, the copolymers have an intrinsic viscosity in tetrahydrofuran of at least about 4.5.

The copolymer compositions prepared with the catalyst described herein may also be characterized in terms of percent relaxation as determined by a procedure which will be discussed more fully below. In one embodiment, the compositions are characterized by percent relaxation values of at least about 30% to about 100%, and more particularly, relaxations of from about 30% to about 70%.

The high molecular weight copolymer compositions also may be characterized as having a dilute solution viscosity in toluene of at least about 3.5 dl/g, and in one embodiment, the copolymers have a dilute solution viscosity of at least about 4.0 dl/g. The copolymers also generally will be characterized by an $\overline{M}w/\overline{M}n$ ratio of at least about 1.3.

The copolymers of a conjugated diene and an aromatic vinyl compound are prepared by polymerizing the mixture in a hydrocarbon solvent in the presence of the above-described polymetalated 1-alkyne catalyst composition. The polymerization temperature may range from about 0° C. to about 160° C. or higher, but generally, the polymerization is conducted at a temperature of between about 75° C. and 150° C. for a period of from about 10 minutes to about 2 or 3 hours. In a preferred embodiment, the polymerization is conducted at a temperature in the vicinity of about 100° C. for about 15 minutes to 1 hour.

The amount of catalyst (polymetalated diene-modified composition described above) employed in the preparation of the copolymers is determined by the desired molecular weight of the copolymer. In one embodiment, the number of moles of catalyst charged to the reactor is determined on a basis of 100 g of monomer(s) and can be calculated by dividing 100 by the desired molecular weight. For example, if a molecular weight of 500,000 is desired, 0.0002 moles (100 divided by 500,000), or 0.20 millimoles of catalyst would be charged to the reactor for every 100 g of monomer (s) in the reactor.

Samples may be withdrawn from the reactor periodically during the polymerization reaction to determine percent conversion (by measuring the total solids), color and character of the reaction mass. The reaction time of the polymerization is dependent upon several factors including the polymerization temperature, the amount of polar modifier (e.g., 2,2'-di(tetrahydrofuryl)propane) and the catalyst concentration. Generally complete conversion to polymer can be obtained at temperatures of about 100° C. in about 15 minutes to 1 hour.

When the polymerization reaction has progressed to the desired degree, the product can be dropped from the reactor or combined with an alcohol such as methanol or isopropanol, or other liquid medium which deactivates the initiator and coagulates and precipitates the polymer product. Generally, an amount of isopropanol equal in weight to the amount of diluent (e.g., hexane) used is sufficient to effect coagulation and precipitation. It is also customary and advantageous to include an antioxidant such as about 1% of di-tertiary butyl para-cresol in the isopropanol. The copolymer product is recovered and dried to remove solvent.

Unless specifically stated otherwise, the molecular weights for the copolymers described herein, are determined by gel permeation chromatography (GPC) according to techniques well-known to those skilled in the art using equipment, software and procedures supplied by Waters Chromatography Division, Millipore Corporation, 34 Maple Street, Milford, Mass., 01757 U.S.A. Determinations are made using organic preparative-grade PL gel (cross-linked polystyrene) columns. Samples of the polymers are dissolved in tetrahydrofuran (THF) stabilized with an antioxidant such as dibutylparacresol and injected into a GPC apparatus equipped with four metal-clad columns. In particular, GPC molecular weight determination with the copolymers of the present invention is made using a Model 200 Waters Gel Permeation Chromatograph retrofitted with a Waters 510 pump, a R-410 Differential Refractometer, and a Waters Wisp Injector System. Four Polymer Laboratories PL gel columns are used, all 7.5 mm. Diameter×300 mm. Long, and packed with crosslinked polystyrene/divinylbenzene, successively having nominal pore sizes of $10^6$, $10^5$, $10^4$ and $10^3$ Angstroms. Polymer samples (0.005 gram) are placed in a flask with 10 ml. of stabilized THF, stoppered, and allowed to stand overnight to complete solution of the polymer. The samples are then filtered through syringe filters of 0.45 micron pore size. A 200 µl. sample of the THF-polymer solution is selected and a run time of 33 minutes used. The flow rate of THF through the chromatograph is set at 1.5 ml. per minute, and after equilibrium is obtained, the copolymer sample solutions are injected. Samples are chromatographed at room temperature and detection of the eluted polymer fractions made by refractometer measurements made at 32° C. Overlapping injection at two-hour intervals is used; this is accomplished using two data collection interfaces. The molecular weight separation which is obtained is measured with the Differential Refractometer, and calculations of molecular weight parameters are carried out using computer programs. The software used in these determinations is Waters Millennium multi-system software. Universal Calibration is carried out with narrow distribution polystyrene standards obtained from Pressure Chemical Corporation.

The dilute solution viscosity (DSV) in toluene of the copolymers is determined as follows. The weighed sample of the copolymer is placed in a 4-ounce bottle and the exact weight ($W_1$) is determined. Toluene (100 ml.) Is added using a pipet, and the bottle is capped securely. The resulting solution is allowed to stand at room temperature for about 18 hours whereupon the mixture is shaken vigorously and filtered through 802 filter paper. A portion (10 ml.) Of the filtrate is pipetted into a tared aluminum pan, and the solvent is evaporated on a hot plate followed by drying in an oven maintained at 105° C. for 10 minutes. The weight of the dried sample is determined, and drying is continued until the residue (liquid copolymer) shows a constant weight ($W_2$). The efflux times of the solvent (toluene) and of the filtered solution (residue) are determined utilizing a 53110/I Schott Gerate Ubbelohde micro viscometer with programmed computer. The viscometer is placed in a constant temperature bath (25° C.) for determination of the efflux times. The programmed computer automatically calculates the DSV and the percent gel of the filtered solution based on the following formulae $$DSV = \frac{Ln(\text{solution flow time/solvent flow time})}{W_2 \times 10}$$

percent gel = $1 - (W_2 \times 10/W_1) \times 100$

The intrinsic viscosity ($\eta$) of the copolymers is determined by the general procedure utilized for DSV except that the intrinsic viscosity is the average of four data points obtained with four different concentrations.

The glass transition temperature (Tg) of the copolymers is determined using a DuPont 1090 thermal analyzer with a 910 Differential Scanning Colorimeter System and following the manufacturer's recommended procedure. The onset, infection and offset temperatures are calculated in accordance with the Interactive DSC Data Analysis-Program V2D.

The relaxation properties of the copolymers are determined using a Bendix Scott STI/200 Mooney Viscometer and a modification of the conventional method for measuring the "shearing viscosity" of rubber and rubber-like materials such as SBR. In this procedure, the sample is placed between the platens which are then closed. The sample is warmed at 100° C. for one minute, and the rotor is turned on. After four minutes, the Mooney value ($ML_{1+4}$) is determined and the rotor is turned off. Measurement of the relaxation is begun, and a relaxation time ($AL_{80}$) is recorded when the torque reaches 20% ($T_{80}$) of the Mooney value $ML_{1+4}$. After a total of 10 minutes, the torque is again observed and recorded as $Al_{1+4+5}$, and the platens are opened. The percent relaxation is calculated as follows:

$$\text{Percent relaxation} = \frac{AL_{1+4+5}}{ML_{1+4}} \times 100$$

The following examples illustrate the use of the catalyst compositions prepared by the method of the invention as catalysts in preparing copolymers of styrene and 1,3-butadiene.

EXAMPLE P-1

To a 100-gallon, nitrogen-filled stainless steel reactor is charged 115.7 kg. of dry hexane, 29.8 kg. of 33% styrene in hexane and 36.4 kg. of 33% solution of 1,3-butadiene in hexane. This mixture is stirred and heated by increasing the reactor jacket temperature to 50° C. (122° F.). When the temperature of the mixture reaches about 43° C. (110° F.), a modifier (76.2 grams of 2,2'-di(tetrahydrofuryl) propane) and 155.3 grams of the product of Example 1 are added. The mixture is exothermic to about 75° C. (168° F.), and the jacket temperature is maintained at 60° C. for one hour. The mixture is cooled to room temperature and 225 grams of water and 318 grams of antioxidant (Santoflex 13) are added. The copolymer is isolated by steam desolventization and oven-drying. The analysis of the resulting polymer is as follows:

| | |
|---|---|
| % Styrene | 49.9 |
| % 1,2-butadiene | 60.6 |
| Tg | −10.5° C. |
| Mn | 456,964 |
| Mw | 708,824 |
| Mw/Mn | 1.55 |

Analysis by gas chromatography indicates 100% styrene and 97.4% butadiene conversions.

EXAMPLE P-2

To a 1000 gallon, nitrogen-filled stainless steel reactor is charged 1241.4 kg. of dry hexane, 258.9 kg. of 33% styrene in hexane and 450.4 kg. of 33% 1,3-butadiene in hexane. This mixture is stirred and heated by increasing the reactor jacket temperature to 63° C. (145° F.). When the mixture of the reactor reaches a temperature of about 43° C. (110° F.), 161.2 grams of 2,2'-di(tetrahydrofuryl) propane and 1.69 kg. of the catalyst product obtained in Example 2 are added. The reaction mixture exotherms to a temperature of 103° C. (217° F.), and the jacket temperature is reduced to 49° C. (120° F.) 30 minutes after the peak temperature is achieved. The reaction product is cooled to room temperature whereupon 2.4 kg. of water and 3.5 kg. of antioxidant (Santoflex 13) are added. The polymer is isolated by steam desolventization and oven drying. The resulting copolymer analyzes as follows:

| % Styrene | 37.8 |
|---|---|
| % 1,2-butadiene | 46.1 |
| Tg | −23.0° C. |
| Mn | 562,637 |
| Mw | 872,087 |
| Mw/Mn | 1.55 |

In this polymerization, 99.8% butadiene and 100% styrene conversions to polymer are attained.

EXAMPLE P-3

To a 10 gallon, nitrogen-filled stainless steel reactor is charged 12.4 kg. of dry hexane, 2.6 kg. of 33% styrene in hexane and 2.5 kg. of 33% 1,3-butadiene in hexane. The mixture is stirred and heated by increasing the reactor jacket temperature to about 63° C. At about 43° C., 1.55 grams of 2,2'-di(tetrahydrofuryl) propane and 16.5 grams of the catalyst product described in Example 3 are added. The mixture exotherms to about 75° C., and 30 minutes after peak temperature is achieved, the jacket temperature is reduced to 49° C. After cooling the reaction product to room temperature, water and antioxidant are added and the polymer is isolated by drum drying. The resulting copolymer (greater than 99% conversion) analyzes as follows:

| % Styrene | 39.7 |
|---|---|
| % 1,2-butadiene | 53.5 |
| Tg | −13° C. |
| Mn | 363,895 |
| Mw | 1,813,347 |
| Mw/Mn | 4.98 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A method of preparing a hydrocarbon-soluble polymetalated composition which comprises the steps of:
   (A) preparing an intermediate by reacting (A-1) an allenic compound of the formula $R^2$—CH=C=$CH_2$ wherein $R^2$ is hydrogen or an aliphatic group containing from 1 to about 10 carbon atoms with (A-2) an organometallic compound $R^o$M in a mole ratio of about 1:2 to about 1:6 wherein $R^o$ is a hydrocarbyl group and M is an alkali metal; and
   (B) reacting said intermediate with a 1,3-conjugated diene wherein the mole ratio of the 1,3-conjugated diene to the allenic compound is at least about 2:1.

2. The method of claim 1 wherein $R^2$ is an aliphatic group containing from 1 to about 4 carbon atoms.

3. The method of claim 1 wherein $R^2$ is methyl.

4. The method of claim 1 wherein the alkali metal is lithium.

5. The method of claim 1 wherein $R^o$ is an alkyl group containing from 1 to about 10 carbon atoms.

6. The method of claim 1 wherein the 1,3-conjugated diene is an aliphatic, 1,3-diene.

7. The method of claim 1 wherein the 1,3-conjugated diene is 1,3-butadiene, isoprene or piperylene.

8. The method of claim 1 wherein the mole ratio of 1,3-conjugated diene to the allenic compound is from about 8:1 to about 20:1.

9. The method of claim 1 wherein the 1,3-conjugated diene is 1,3 butadiene.

10. A method of preparing a hydrocarbon-soluble polymetalated composition which comprises the steps of:
    (A) preparing an intermediate by reacting (A-1) an allenic compound of the formula $R^2$—CH=C=$CH_2$ wherein $R^2$ is hydrogen or an aliphatic hydrocarbyl group containing from 1 to about 4 carbon atoms with (A-2) an organolithium compound $R^o$Li in a mole ratio of from about 1:2 to about 1:6 wherein $R^o$ is an aliphatic group containing from 1 to about 5 carbon atoms; and
    (B) reacting said intermediate with a 1,3-conjugated diene wherein the mole ratio of the 1,3-conjugated diene to the allenic compound is at least about 2:1.

11. The method of claim 10 wherein the allenic compound is 1,2-butadiene.

12. The method of claim 10 wherein $R^o$ is n-butyl.

13. The method of claim 10 wherein the 1,3-conjugated diene is 1,3-butadiene, isoprene or piperylene.

14. The method of claim 10 where the mole ratio of the conjugated diene to allenic compound is from about 8:1 to about 20:1.

15. A method of preparing a hydrocarbon-soluble polylithiated composition which comprises the steps of:
    (A) preparing an intermediate by reacting (A-1) 1,2-butadiene with (A-2) an organolithium compound $R^o$Li in a mole ratio of from about 1:3 to about 1:4 wherein $R^o$ is an aliphatic group containing from 1 to about 4 carbon atoms; and
    (B) reacting one mole of said intermediate with from about 8 to about 20 moles of 1,3-butadiene.

16. The method of claim 15 wherein the reaction in step (A) is conducted in a hydrocarbon solvent.

17. A composition comprising a mixture of one or more polymetalated 1-alkynes and one or more polymetalated allene compounds wherein the 1-alkynes are characterized by the formula

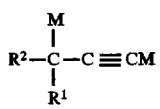

(I)

wherein $R^2$ is hydrogen, a hydrocarbyl group or M, $R^1$ is hydrogen or M, and M is an alkali metal, and the allene compound is characterized by the formula

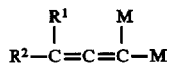

(II)

wherein $R^2$ is hydrogen, a hydrocarbyl group or M, and $R^1$ is hydrogen or M, and M is an alkali metal.

18. The composition of claim 17 wherein in Formula I, $R^2$ is a hydrocarbyl group and $R^1$ is hydrogen or M.

19. The composition of claim 17 wherein in Formula II, $R^2$ is a hydrocarbyl group and $R^1$ is hydrogen or M.

20. The composition of claim 17 wherein M is lithium.

21. The composition of claim 17 wherein in Formula I, $R^2$ is methyl and $R^1$ is hydrogen or M.

22. A hydrocarbon-soluble composition comprising a mixture of one or more polymetalated 1-alkynes and one or more polymetalated allenes wherein the alkyne is represented by the formula $$R^2-\underset{\underset{R^4}{|}}{\overset{\overset{R^3M}{|}}{C}}-C\equiv CM \qquad (III)$$

wherein $R^2$ is hydrogen, a hydrocarbyl group or R3M, $R^4$ is hydrogen or R3M, M is an alkali metal and $R^3$ is a divalent oligomeric hydrocarbyl group comprising moieties derived from a conjugated diene, and the allene is characterized by the formula $$R^2-\underset{\underset{R^4}{|}}{C}=C=\underset{\underset{R^3M}{|}}{C}-R^3M \qquad (IV)$$

wherein $R^2$ is hydrogen, a hydrocarbyl group or R3M, $R^4$ is hydrogen or R3M, M is an alkali metal and each $R^3$ is independently a divalent oligomeric hydrocarbyl group comprising moieties derived from a conjugated diene.

23. The composition of claim 22 wherein the composition comprises a mixture of polymetalated 1-alkynes represented by Formula III wherein $R^4$ is hydrogen or $R^3M$ and R is a hydrocarbyl group.

24. The composition of claim 22 wherein $R^2$ is a hydrocarbyl group containing from 1 to about 5 carbon atoms and M is lithium.

25. A method for preparing copolymer compositions of 1,3-conjugated dienes and aromatic vinyl compounds which comprises polymerizing a 1,3-conjugated diene and a vinyl aromatic compound in a hydrocarbon solvent in the presence of the, composition of claim 22.

26. The method of claim 25 wherein M is lithium.

27. The method of claim 25 wherein $R^3$ is derived from an alkadiene containing from 4 to about 12 carbon atoms.

28. The method of claim 25 wherein the total number of conjugated diene-derived moieties in all of the $R^3$ groups is from about 8 to about 20, and the conjugated diene is 1,3-butadiene.

* * * * *